(12) United States Patent
O'Phelan et al.

(10) Patent No.: US 7,365,960 B2
(45) Date of Patent: Apr. 29, 2008

(54) CAPACITOR HAVING A FEEDTHROUGH ASSEMBLY WITH A COUPLING MEMBER

(75) Inventors: Michael J. O'Phelan, Oakdale, MN (US); Richard J. Kavanagh, Brooklyn Park, MN (US); James M. Poplett, Plymouth, MN (US); A. Gordon Barr, Burnsville, MN (US); Brian D. Schenk, Coon Rapids, MN (US); Brian L. Schmidt, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/668,109

(22) Filed: Jan. 29, 2007

(65) Prior Publication Data

US 2007/0118182 A1 May 24, 2007

Related U.S. Application Data

(62) Division of application No. 10/846,805, filed on May 14, 2004, now Pat. No. 7,177,692, which is a division of application No. 09/706,579, filed on Nov. 3, 2000, now Pat. No. 7,107,099.

(51) Int. Cl.
*H01G 9/04* (2006.01)

(52) U.S. Cl. .............. 361/508; 361/509; 361/516; 361/519; 361/523; 361/525; 361/528

(58) Field of Classification Search ........ 361/508–509, 361/516–519, 523–534, 502–504; 607/5, 607/7
See application file for complete search history.

(56) References Cited

U.S. PATENT DOCUMENTS 1,474,486 A 11/1923 Macpherson
1,931,043 A 10/1933 Taylor
2,555,326 A 6/1951 Doughty, Jr.

(Continued)

FOREIGN PATENT DOCUMENTS

EP 0224733 A1 6/1987

(Continued)

OTHER PUBLICATIONS

Schmidt, Brian L., et al., "Configurations and Methods for Making Capacitor Connections", U.S. Appl. No. 09/706,576, filed Nov. 3, 2000, 26 pgs.

(Continued)

*Primary Examiner*—Nguyen T. Ha
(74) *Attorney, Agent, or Firm*—Schwegman, Lundberg & Woessner, P.A.

(57) ABSTRACT

A flat capacitor includes a case having a feedthrough hole, a capacitor stack located within the case, a coupling member having a base surface directly attached to the capacitor stack and having a portion extending through the feedthrough hole, the coupling member having a mounting hole, a feedthrough conductor having a portion mounted within the mounting hole, and a sealing member adjacent the feedthrough hole and the feedthrough conductor for sealing the feedthrough hole. Other aspects of the invention include various implantable medical devices, such as pacemakers, defibrillators, and cardioverters, incorporating one or more features of the exemplary feedthrough assembly.

17 Claims, 5 Drawing Sheets

U.S. PATENT DOCUMENTS

| | | |
|---|---|---|
| 3,150,301 A | 9/1964 | Schils et al. |
| 3,389,311 A | 6/1968 | Rayno |
| 3,424,857 A | 1/1969 | Miller et al. |
| 3,643,168 A | 2/1972 | Manicki |
| 3,686,535 A | 8/1972 | Piper |
| 3,686,538 A | 8/1972 | Webster |
| 3,723,926 A | 3/1973 | Thomas et al. |
| 3,777,570 A | 12/1973 | Thomas et al. |
| 3,803,457 A | 4/1974 | Yamamoto |
| 3,826,143 A | 7/1974 | Thomas et al. |
| 3,828,227 A | 8/1974 | Millard et al. |
| 3,859,574 A | 1/1975 | Brazier |
| 3,938,228 A | 2/1976 | Kemkers et al. |
| 4,045,644 A | 8/1977 | Shafer et al. |
| 4,047,790 A | 9/1977 | Carino |
| 4,086,148 A | 4/1978 | Badia |
| 4,088,108 A | 5/1978 | Hager |
| 4,131,935 A | 12/1978 | Clement |
| 4,171,477 A | 10/1979 | Funari |
| 4,247,883 A | 1/1981 | Thompson et al. |
| 4,267,565 A | 5/1981 | Puppolo et al. |
| 4,307,142 A | 12/1981 | Blitstein et al. |
| 4,394,713 A | 7/1983 | Yoshida |
| 4,571,662 A | 2/1986 | Conquest et al. |
| 4,782,340 A | 11/1988 | Czubatyj et al. |
| 4,931,899 A | 6/1990 | Pruett |
| 5,041,942 A | 8/1991 | Carrico |
| 5,131,388 A | 7/1992 | Pless et al. |
| 5,333,095 A | 7/1994 | Stevenson et al. |
| 5,377,073 A | 12/1994 | Fukaumi et al. |
| 5,439,760 A | 8/1995 | Howard et al. |
| 5,471,087 A | 11/1995 | Buerger, Jr. |
| 5,507,966 A | 4/1996 | Liu |
| 5,522,851 A | 6/1996 | Fayram |
| 5,527,346 A | 6/1996 | Kroll |
| 5,554,178 A | 9/1996 | Dahl et al. |
| 5,584,890 A | 12/1996 | MacFarlane et al. |
| 5,628,801 A | 5/1997 | MacFarlane et al. |
| 5,634,938 A | 6/1997 | Swanson et al. |
| 5,658,319 A | 8/1997 | Kroll |
| 5,660,737 A | 8/1997 | Elias et al. |
| 5,716,729 A | 2/1998 | Sunderland et al. |
| 5,754,394 A | 5/1998 | Evans et al. |
| 5,779,699 A | 7/1998 | Lipson |
| 5,779,891 A | 7/1998 | Andelman |
| 5,800,724 A | 9/1998 | Habeger et al. |
| 5,801,917 A | 9/1998 | Elias |
| 5,814,082 A | 9/1998 | Fayram et al. |
| 5,867,363 A | 2/1999 | Tsai et al. |
| 5,901,867 A | 5/1999 | Mattson |
| 5,908,151 A | 6/1999 | Elias |
| 5,922,215 A | 7/1999 | Pless et al. |
| 5,926,357 A | 7/1999 | Elias et al. |
| 5,926,362 A | 7/1999 | Muffoletto et al. |
| 5,930,109 A | 7/1999 | Fishler |
| 5,949,638 A | 9/1999 | Greenwood, Jr. et al. |
| 5,950,131 A | 9/1999 | Vilmur |
| 5,963,418 A | 10/1999 | Greenwood, Jr. et al. |
| 5,968,210 A | 10/1999 | Strange et al. |
| 5,973,906 A | 10/1999 | Stevenson et al. |
| 5,983,472 A | 11/1999 | Fayram et al. |
| 6,002,969 A | 12/1999 | Machek et al. |
| 6,006,133 A | 12/1999 | Lessar et al. |
| 6,009,348 A | 12/1999 | Rorvick et al. |
| 6,032,075 A | 2/2000 | Pignato et al. |
| 6,040,082 A | 3/2000 | Haas et al. |
| 6,042,624 A | 3/2000 | Breyen et al. |
| 6,052,625 A | 4/2000 | Marshall |
| 6,094,788 A | 8/2000 | Farahmandi et al. |
| 6,099,600 A | 8/2000 | Yan et al. |
| 6,104,961 A | 8/2000 | Conger et al. |
| 6,110,233 A | 8/2000 | O'Phelan et al. |
| 6,117,194 A | 9/2000 | Strange et al. |
| 6,118,651 A | 9/2000 | Mehrotra et al. |
| 6,141,205 A | 10/2000 | Nutzman et al. |
| 6,157,531 A | 12/2000 | Breyen et al. |
| 6,184,160 B1 | 2/2001 | Yan et al. |
| 6,191,931 B1 | 2/2001 | Paspa et al. |
| 6,212,063 B1 | 4/2001 | Johnson et al. |
| 6,249,423 B1 | 6/2001 | O'Phelan et al. |
| 6,249,709 B1 | 6/2001 | Conger et al. |
| 6,256,542 B1 | 7/2001 | Marshall et al. |
| 6,259,954 B1 | 7/2001 | Conger et al. |
| 6,275,372 B1 | 8/2001 | Vassallo et al. |
| 6,275,729 B1 | 8/2001 | O'Phelan et al. |
| 6,283,985 B1 * | 9/2001 | Harguth et al. ................. 607/1 |
| 6,297,943 B1 | 10/2001 | Carson |
| 6,299,752 B1 | 10/2001 | Strange et al. |
| 6,321,114 B1 | 11/2001 | Nutzman et al. |
| 6,324,049 B1 | 11/2001 | Inagawa et al. |
| 6,326,587 B1 | 12/2001 | Cardineau et al. |
| 6,375,688 B1 | 4/2002 | Akami et al. |
| 6,380,577 B1 | 4/2002 | Cadwallader |
| 6,388,866 B1 | 5/2002 | Rorvick et al. |
| 6,402,793 B1 | 6/2002 | Miltich et al. |
| 6,409,776 B1 | 6/2002 | Yan et al. |
| 6,442,015 B1 | 8/2002 | Niiori et al. |
| 6,451,073 B1 | 9/2002 | Farahmandi et al. |
| 6,477,037 B1 | 11/2002 | Nielsen et al. |
| 6,493,212 B1 | 12/2002 | Clarke et al. |
| 6,509,588 B1 | 1/2003 | O'Phelan et al. |
| 6,522,525 B1 | 2/2003 | O'Phelan et al. |
| 6,556,863 B1 | 4/2003 | O'Phelan et al. |
| 6,571,126 B1 | 5/2003 | O'Phelan et al. |
| 6,585,152 B2 | 7/2003 | Farahmandi et al. |
| 6,628,505 B1 | 9/2003 | Andelman |
| 6,674,634 B2 | 1/2004 | O'Phelan et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,763,265 B2 | 7/2004 | O'Phelan et al. |
| 6,795,729 B1 | 9/2004 | Breyen et al. |
| 6,833,987 B1 | 12/2004 | O'Phelan |
| 6,885,548 B2 | 4/2005 | Nyberg |
| 6,885,887 B2 | 4/2005 | O'Phelan et al. |
| 6,957,103 B2 | 10/2005 | Schmidt et al. |
| 6,985,351 B2 | 1/2006 | O'Phelan et al. |
| 6,990,375 B2 | 1/2006 | Kloss et al. |
| 6,999,304 B2 | 2/2006 | Schmidt et al. |
| 7,072,713 B2 | 7/2006 | O'Phelan et al. |
| 7,079,897 B2 | 7/2006 | Sun et al. |
| 7,107,099 B1 | 9/2006 | O'Phelan et al. |
| 7,120,008 B2 | 10/2006 | Sherwood |
| 7,154,739 B2 | 12/2006 | O'Phelan |
| 7,157,671 B2 | 1/2007 | O'Phelan et al. |
| 7,177,692 B2 | 2/2007 | O'Phelan et al. |
| 7,180,727 B2 | 2/2007 | Poplett |
| 7,190,569 B2 | 3/2007 | O'Phelan et al. |
| 7,190,570 B2 | 3/2007 | Schmidt et al. |
| 7,221,556 B2 | 5/2007 | Schmidt et al. |
| 2003/0072124 A1 | 4/2003 | O'Phelan et al. |
| 2003/0195568 A1 | 10/2003 | O'Phelan et al. |
| 2004/0019268 A1 | 1/2004 | Schmidt et al. |
| 2004/0114311 A1 | 6/2004 | O'Phelan et al. |
| 2004/0127952 A1 | 7/2004 | O'Phelan et al. |
| 2004/0193221 A1 | 9/2004 | O'Phelan et al. |
| 2005/0017888 A1 | 1/2005 | Sherwood et al. |
| 2005/0052825 A1 | 3/2005 | O'Phelan |
| 2006/0009808 A1 | 1/2006 | Schmidt et al. |
| 2006/0012942 A1 | 1/2006 | Poplett |
| 2006/0107506 A1 | 5/2006 | Doffing et al. |
| 2006/0152887 A1 | 7/2006 | Schmidt et al. |
| 2006/0174463 A1 | 8/2006 | O'Phelan et al. |

| | | |
|---|---|---|
| 2006/0247715 A1 | 11/2006 | Youker |
| 2006/0257726 A1 | 11/2006 | Kelley et al. |

FOREIGN PATENT DOCUMENTS

| | | |
|---|---|---|
| GB | 825900 | 12/1959 |
| GB | 2132019 | 6/1984 |
| JP | 05-074664 | 3/1993 |
| WO | WO-98/27562 | 6/1998 |
| WO | WO-99/51302 | 10/1999 |
| WO | WO-9951302 A1 | 10/1999 |
| WO | WO-00/19470 | 4/2000 |
| WO | WO-0237515 A2 | 5/2002 |
| WO | WO-2006002148 A1 | 1/2006 |

OTHER PUBLICATIONS

"U.S. Appl. No. 09/706,447 Non Final Office Action mailed Mar. 26, 2003", 9 pgs.

"U.S. Appl. No. 09/706,447 Notice of Allowance mailed Sep. 23, 2003", 6 pgs.

"U.S. Appl. No. 09/706,447 Response filed Jun. 25, 2003 to Non Final Office Action mailed Mar. 26, 2003", 10 pgs.

"U.S. Appl. No. 09/706,517 Non Final Office Action mailed Apr. 23, 2003", 15 pgs.

"U.S. Appl. No. 09/706,517 Non Final Office Action mailed Dec. 15, 2003", 10 pgs.

"U.S. Appl. No. 09/706,517 Notice of Allowance mailed Jul. 1, 2004", 8 pgs.

"U.S. Appl. No. 09/706,517 Response filed Mar. 15, 2004 to Non Final Office Action mailed Dec. 15, 2003", 11 pgs.

"U.S. Appl. No. 09/706,517 Response filed Aug. 25, 2003 to Non Final Office Action mailed Apr. 23, 2003", 13 pgs.

"U.S. Appl. No. 09/706,518 Non Final Office Action mailed Mar. 24, 2003", 9 pgs.

"U.S. Appl. No. 09/706,518 Non Final Office Action mailed Apr. 18, 2002", 13 pgs.

"U.S. Appl. No. 09/706,518 Non Final Office Action mailed Oct. 4, 2002", 9 pgs.

"U.S. Appl. No. 09/706,518 Notice of Allowance mailed Sep. 9, 2003", 10 pgs.

"U.S. Appl. No. 09/706,518 Response filed Jan. 6, 2003 to Non Final Office Action mailed Oct. 4, 2002", 4 pgs.

"U.S. Appl. No. 09/706,518 Response filed Jun. 24, 2003 to Non Final Office Action mailed Mar. 24, 2003", 9 pgs.

"U.S. Appl. No. 09/706,518 Response filed Jul. 18, 2002 to Non Final Office Action mailed Apr. 18, 2002", 7 pgs.

"U.S. Appl. No. 09/706,576, Supplemental Notice of Allowability Mailed Sep. 6, 2007", 4 pgs.

"U.S. Appl. No. 09/706,576, Amendment and Response filed Jun. 12, 2003 to Notice of Non-Compliant Amendment mailed May 12, 2003", 12 pgs.

"U.S. Appl. No. 09/706,576, Notice of Non-Compliant Amendment mailed May 12, 2003", 2 pgs.

"U.S. Appl. No. 09/706,576 Amendment and Response Under 37 CFR 1.116 mailed Oct. 12, 2004", 10 pgs.

"U.S. Appl. No. 09/706,576 Final Office Action mailed Sep. 10, 2003", 6 pgs.

"U.S. Appl. No. 09/706,576 Final Office Action mailed Oct. 5, 2005", 13 pgs.

"U.S. Appl. No. 09/706,576 Non Final Office Action mailed Jan. 10, 2005", 12 pgs.

"U.S. Appl. No. 09/706,576 Non Final Office Action mailed Feb. 2, 2007", 7 pgs.

"U.S. Appl. No. 09/706,576 Non Final Office Action mailed Oct. 31, 2002", 8 pgs.

"U.S. Appl. No. 09/706,576 Notice of Allowance mailed Jul. 18, 2007", NOAR,5 pgs.

"U.S. Appl. No. 09/706,576 Response filed Apr. 30, 2003 to Non Final Office Action mailed Oct. 31, 2002", 12 pgs.

"U.S. Appl. No. 09/706,576 Response filed Jul. 2, 2007 to Non Final Office Action mailed Feb. 2, 2007", 5 pgs.

"U.S. Appl. No. 09/706,576 Response filed Jul. 11, 2005 to Non Final Office Action mailed Jan. 10, 2005", 12 pgs.

"U.S. Appl. No. 09/706,576 Response filed Nov. 6, 2006 to Final Office Action mailed Oct. 5, 2005", 6 pgs.

"U.S. Appl. No. 09/706,579 Non Final Office Action mailed Mar. 7, 2003", 9 pgs.

"U.S. Appl. No. 09/706,579 Non Final Office Action mailed Oct. 3, 2003", 7 pgs.

"U.S. Appl. No. 09/706,579 Notice of Allowance mailed Feb. 4, 2004", 5 pgs.

"U.S. Appl. No. 09/706,579 Notice of Allowance mailed Mar. 4, 2005", 21 pgs.

"U.S. Appl. No. 09/706,579 Notice of Allowance mailed Apr. 6, 2006", 17 pgs.

"U.S. Appl. No. 09/706,579 Notice of Allowance mailed Sep. 9, 2005", 9 pgs.

"U.S. Appl. No. 09/706,579 Response filed Jul. 7, 2003 to Non Final Office Action mailed Mar. 7, 2003", 9 pgs.

"U.S. Appl. No. 09/706,579 Response filed Dec. 30, 2003 to Non Final Office Action mailed Oct. 3, 2003", 9 pgs.

"U.S. Appl. No. 10/413,680 Non Final Office Action mailed May 21, 2004", 6 pgs.

"U.S. Appl. No. 10/413,680 Non Final Office Action mailed Nov. 18, 2004", 11 pgs.

"U.S. Appl. No. 10/413,680 Notice of Allowance mailed May 3, 2005", 5 pgs.

"U.S. Appl. No. 10/413,680 Response filed Feb. 18, 2005 to Non Final Office Action mailed Nov. 18, 2004", 9 pgs.

"U.S. Appl. No. 10/413,680 Response filed Aug. 23, 2004 to Non Final Office Action mailed May 21, 2004", 9 pgs.

"U.S. Appl. No. 10/758,677 Final Office Action mailed May 17, 2006", 7 pgs.

"U.S. Appl. No. 10/758,677 Non Final Office Action mailed Feb. 9, 2005", 5 pgs.

"U.S. Appl. No. 10/758,677 Non Final Office Action mailed Jul. 13, 2004", 12 pgs.

"U.S. Appl. No. 10/758,677 Non Final Office Action mailed Nov. 16, 2005", 5 pgs.

"U.S. Appl. No. 10/758,677 Notice of Allowance mailed Aug. 24, 2006", 16 pgs.

"U.S. Appl. No. 10/758,677 Response filed Feb. 16, 2006 to Non Final Office Action mailed Nov. 16, 2005", 9 pgs.

"U.S. Appl. No. 10/758,677 Response filed Jul. 17, 2006 to Final Office Action mailed May 17, 2006", 9 pgs.

"U.S. Appl. No. 10/758,677 Response filed Aug. 9, 2005 to Non Final Office Action mailed Feb. 9, 2005", 9 pgs.

"U.S. Appl. No. 10/758,677 Response filed Nov. 15, 2004 to Non Final Office Action mailed Jul. 13, 2004", 9 pgs.

"U.S. Appl. No. 10/758,701 Non Final Office Action mailed Aug. 9, 2005", 7 pgs.

"U.S. Appl. No. 10/758,701 Notice of Allowance mailed Jan. 25, 2006", 7 pgs.

"U.S. Appl. No. 10/758,701 Response filed Nov. 9, 2005 to Non Final Office Action mailed Aug. 9, 2005", 8 pgs.

"U.S. Appl. No. 10/846,805 Non Final Office Action mailed Apr. 19, 2006", 14 pgs.

"U.S. Appl. No. 10/846,805 Notice of Allowance mailed Sep. 27, 2006", 7 pgs.

"U.S. Appl. No. 10/846,805 Preliminary Amendment filed May 14, 2004", 6 pgs.

"U.S. Appl. No. 10/846,805 Response filed Jul. 19, 2006 to Non Final Office Action mailed Apr. 19, 2006", 8 pgs.

"U.S. Appl. No. 10/969,441 Non Final Office Action mailed Apr. 1, 2005", 13 pgs.

"U.S. Appl. No. 10/969,441 Non Final Office Action mailed Sep. 19, 2005", 8 pgs.

"U.S. Appl. No. 10/969,441 Notice of Allowance mailed Mar. 29, 2006", 8 pgs.

"U.S. Appl. No. 10/969,441 Notice of Allowance mailed Sep. 11, 2006", 8 pgs.

"U.S. Appl. No. 10/969,441 Response filed Jun. 29, 2005 to Non Final Office Action mailed Apr. 1, 2005", 7 pgs.

"U.S. Appl. No. 10/969,441 Response filed Dec. 19, 2005 to Non Final Office Action mailed Sep. 19, 2005", 8 pgs.

"U.S. Appl. No. 11/226,954 Non Final Office Action mailed May 17, 2006", 13 pgs.

"U.S. Appl. No. 11/226,954 Non Final Office Action mailed Dec. 15, 2005", 18 pgs.

"U.S. Appl. No. 11/226,954 Notice of Allowance mailed Nov. 1, 2006", 5 pgs.

"U.S. Appl. No. 11/226,954 Response filed Mar. 15, 2006 to Non Final Office Action mailed Dec. 15, 2005", 12 pgs.

"U.S. Appl. No. 11/226,954 Response filed Aug. 17, 2006 to Non Final Office Action mailed May 17, 2006", 8 pgs.

"PCT Application No. PCT/US01/50257, International Search Report mailed Jun. 4, 2003", 6 pgs.

* cited by examiner

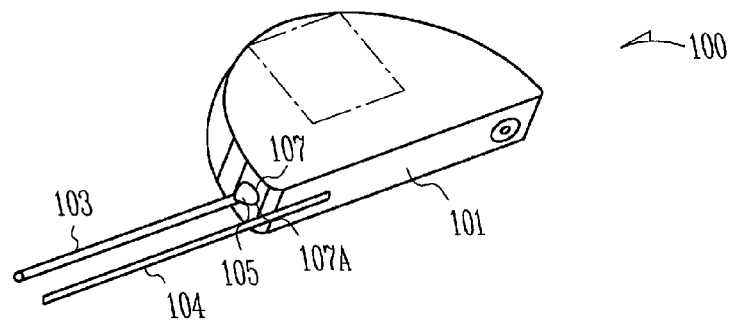
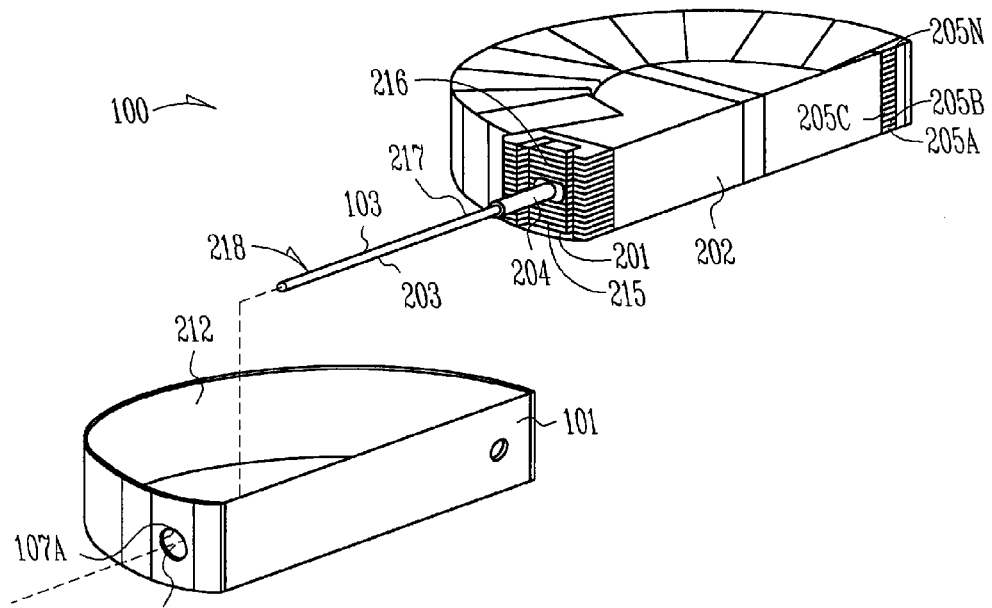
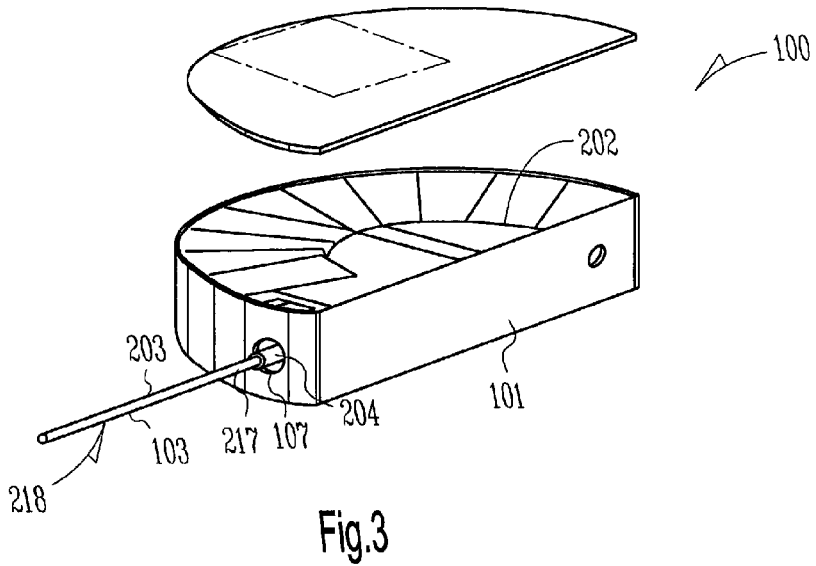

CAPACITOR HAVING A FEEDTHROUGH ASSEMBLY WITH A COUPLING MEMBER

CROSS-REFERENCE TO RELATED APPLICATIONS

This application is a division of application Ser. No. 10/846,805, filed on May 14, 2004, now issued as U.S. Pat. No. 7,177,692, which is a division of application Ser. No. 09/706,579, filed on Nov. 3, 2000, now issued as U.S. Pat. No. 7,107,099, the specifications of which are incorporated herein by reference.

This application is related to application Ser. No. 09/706,447, filed on Nov. 3, 2000, now issued as U.S. Pat. No. 6,699,265, which is incorporated herein by reference in its entirety.

TECHNICAL FIELD

The present invention concerns implantable heart monitors, such as defibrillators and cardioverters, particularly structures and methods for capacitors in such devices.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor can take the form of a flat aluminum electrolytic capacitor. Flat capacitors include a stack of flat capacitor elements, with each element including one or more separators between two sheets of aluminum foil. The capacitor elements, each of which has an individual capacitance (or energy-storage capacity) proportional to the surface area of the aluminum foil, are connected together to provide a total capacitance. The stack of capacitor elements is housed within an aluminum capacitor case which is filled with electrolyte.

The capacitor includes one or more metal wires, known as feedthroughs, which connect the capacitor elements to defibrillator or cardioverter circuitry located outside the case. A feedthrough reaches the outside of the case through a hole in the case called a feedthrough hole. After the capacitor elements are assembled within the capacitor case and the feedthrough is inserted through the feedthrough hole, manufacturers insulate the feedthrough from the case and seal the feedthrough hole. This involves, for instance, assembling an insulating sleeve, a nut, a gasket and/or other hardware around the feedthrough wire.

Thus, assembling the feedthrough, insulating the feedthrough, and sealing the feedthrough is a complex, time-consuming process.

SUMMARY

To address these and other needs, the inventors have devised new capacitor structures and methods. An exemplary capacitor includes a case containing a capacitor stack. A coupling member having a base surface is directly attached to the capacitor stack. A feedthrough conductor has a portion which extends through a feedthrough hole in the case and into a mounting hole in the coupling member. The capacitor includes a sealing member adjacent the feedthrough hole and the feedthrough conductor for sealing the feedthrough hole.

One option provides an exemplary feedthrough assembly which includes a plug having a hole and a feedthrough conductor mounted within the hole. The feedthrough conductor has a diameter approximately equal to or larger than the plug hole diameter, thus sealing the feedthrough hole without requiring any epoxy or excess hardware.

Among other advantages, the relatively uncomplicated feedthrough structure of the exemplary capacitor provides for easier manufacturing and more reliable capacitors. Other facets of the invention include various implantable medical devices, such as pacemakers, defibrillators, and cardioverters, incorporating one or more features of the novel capacitors.

BRIEF DESCRIPTION OF DRAWINGS

FIG. 1 is an isometric view of a flat capacitor in accord with one embodiment of the present invention.

FIG. 2 is an exploded isometric view of the flat capacitor of FIG. 1.

FIG. 3 is another exploded isometric view of the flat capacitor of FIG. 1.

DETAILED DESCRIPTION

Figure 4:
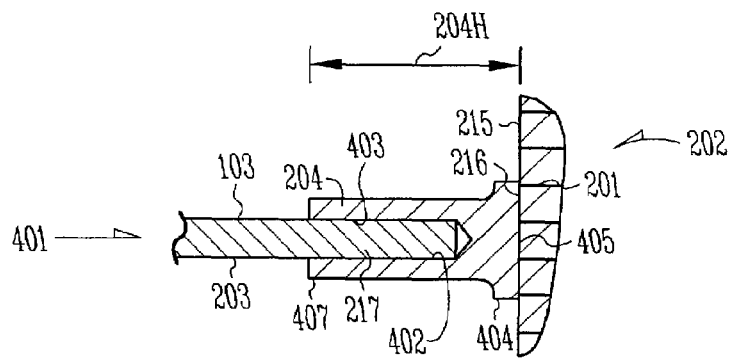
FIG. 4 is a cross-sectional view of the feedthrough assembly of FIG. 1.

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

FIG. 1 shows a flat capacitor 100 in accord with one embodiment of the present invention. Capacitor 100 includes a case 101, a feedthrough assembly 103, a terminal 104, and a sealing member 105. In the exemplary embodiment, case 101 is a D-shaped container manufactured from a conductive material, such as aluminum. In other embodiments, case 101 is rectangular, circular, oval, or other desirable symmetrical or asymmetrical shape. Also, in some embodiments, case 101 is manufactured from a nonconductive material, such as a ceramic or a plastic.

Case 101 includes a feedthrough hole 107 which is drilled, molded, or punched in a portion of a wall of case 101. Feedthrough hole 107 is in part defined by an edge 107a which outlines the feedthrough hole within case 101. Feedthrough hole 107 provides a passage for connecting feedthrough assembly 103 to circuitry outside of case 101. In some embodiments, case 101 includes two or more feedthrough holes for providing a second or third feedthrough assembly.

Feedthrough assembly 103 and terminal 104 connect capacitor elements to outside circuitry. In the exemplary embodiment, feedthrough assembly 103 extends through feedthrough hole 107 and is insulated from case 101. Terminal 104 is directly connected to case 101. Alternatively, in some embodiments, the capacitor incorporates other connection methods, depending on other design factors. In various embodiments, two or more insulated feedthrough assemblies are employed.

In the exemplary embodiment, sealing member 105, such as an epoxy, is deposited around feedthrough hole 107 and feedthrough assembly 103 to insulate feedthrough assembly 103 from case 101 and to seal an electrolyte within the case. An exemplary epoxy is a two-part epoxy manufactured by Dexter Hysol. This includes a casting resin compound (manufacturer No. EE 4183), a casting compound (manufacturer No. EE 4215), and a hardener (manufacturer No. HD 3404). The exemplary two-part epoxy is mixed in a ratio of hardener=0.055*casting resin. The mixture is cured at 0.5 hours at 60 degrees Celsius or 1.5 hours at room temperature. Another exemplary epoxy is a UV cure epoxy such as manufactured by Dymax, Inc., which can be cured using an Acticure (manufactured by GenTec) ultraviolet curing system at 7 W/cm$^2$ at a distance of 0.25" for approximately 10 seconds.

In one embodiment, the sealing member provides a nonhermetic seal. In one embodiment, the sealing member includes an elastic plug which will be discussed in further detail below.

FIGS. 2 and 3 show exploded views of exemplary capacitor 100. Capacitor 100 includes a capacitor stack 202 mounted within an internal cavity 212. The exemplary capacitor stack 202 includes a plurality of capacitor modules or elements 205a, 205b, 205c, . . . , 205n. Each of elements 205a-205n includes a cathode, an anode, and a separator between the cathode and the anode.

Each anode includes one or more anode members in a stack. These anodes and cathodes are foil structures and can be made from aluminum, tantalum, hafnium, niobium, titanium, zirconium, and combinations of these metals. A major surface of each anode foil is roughened to increase its effective surface area. This increases the capacitive effect of the foil with no relative increase in volume. However, none of the embodiments are limited to any particular foil composition or class of foil compositions.

The separators include one or more electrolyte impregnated separators between each anode and each cathode. In the exemplary embodiment, each separator consists of two kraft papers impregnated with an electrolyte. The electrolyte can be any suitable electrolyte for an electrolytic capacitor, such as an ethylene-glycol base combined with polyphosphates, ammonium pentaborate, and/or an adipic acid solute. Other embodiments incorporate different numbers and arrangements of anodes, cathodes, and separators.

In the exemplary embodiment, each cathode of capacitor stack 202 is connected to the other cathodes and to conductive case 101. Terminal 104 is attached to case 101 to provide a cathode connection to outside circuitry. In some embodiments, the cathode is coupled to a feedthrough conductor extending through a feedthrough hole.

In the exemplary embodiment, each anode is connected to the other anodes of the capacitor. Attached to the anode of each capacitor element 205a-205n is a conductive tab or connection member 201. In one embodiment, each connection member 201 includes an edge face 215 which is substantially perpendicular to the major surface of the anodes. Edge face 215 provides a conductive surface for connecting each capacitor element 205a-205n to feedthrough assembly 103. The anode connection members 201 are welded or crimped together and are coupled to feedthrough assembly 103 for electrically connecting the anode to circuitry outside the case. In some embodiments, the cathode is coupled to a feedthrough assembly and the anode is connected to the case. In other embodiments, both the anode and the cathode are connected to feedthroughs.

In one embodiment, connection members 201 are edge-welded to each other as discussed in U.S. patent application Ser. No. 09/706,518, filed Nov. 3, 2000, now issued as U.S. Pat. No. 6,687,118, which is incorporated herein by reference in its entirety. Edge-welding the connection members provides a flat connection surface 216, which includes one or more edge faces 215 of connection members 201. In some embodiments, connection members 201 are crimped, soldered, and/or connected by an electrically conductive adhesive.

In the exemplary embodiment, feedthrough assembly 103 includes two members, a feedthrough wire or conductor 203 and a coupling member 204. Coupling member 204 is attached to capacitor stack 202 at connection surface 216, and feedthrough conductor 203 is attached to coupling member 204. In the exemplary embodiment, coupling member 204 partially extends through feedthrough hole 107.

Feedthrough conductor 203 is a conductive member which can include material such as nickel, gold plated nickel, platinum, aluminum, or other conductive metal. Feedthrough conductor 203 has a proximal end portion 217 attached to coupling member 204 and a distal end portion 218 for attaching to circuitry outside the case, such as defibrillator or cardioverter circuitry. In the exemplary embodiment, feedthrough conductor 203 has a diameter of approximately 0.016" (0.4064 mm). However, other embodiments have feedthrough conductors of different diameters and/or non-circular cross-sections.

FIG. 4 shows a cross-sectional side view of details of one embodiment of feedthrough assembly 103 and its connection to connection members 201. As discussed above, in the exemplary embodiment, the edge faces 215 of each connection member 201 form a substantially flat connection surface 216. In the exemplary embodiment, coupling member 204 is directly attached to connection members 201 at surface 216.

In the exemplary embodiment, coupling member 204 is a high-purity aluminum member which is able to withstand the high voltages generated within the capacitor case. In other embodiments it is made from another conductive material compatible with the capacitor stack. Coupling member 204 includes a base 404 and a holding tube 407. On one side of base 404 is a planar surface 405 for attaching to the planar surface 216 presented by edge-welded connection members 201.

Figures 6, 7:
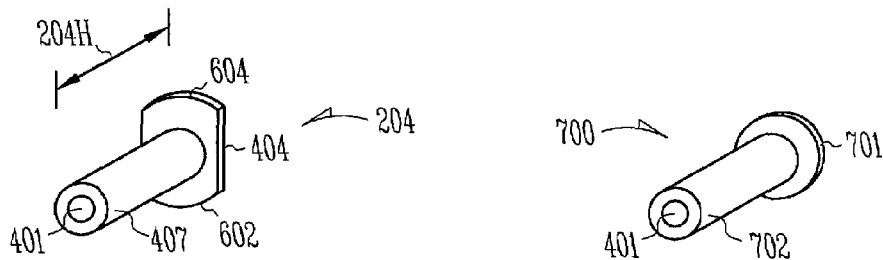
FIG. 6 is an isometric view of an exemplary coupling member in accord with one embodiment of the present invention.
FIG. 7 is an isometric view of another exemplary coupling member in accord with one embodiment of the present invention.

FIG. 6 shows additional details of exemplary base 404. In the exemplary embodiment, base 404 is substantially rectangular having a pair of opposing rounded or curved ends 602 and 604.

Referring again to FIG. 4, in the exemplary embodiment, coupling member 204 is situated so that surface 405 abuts connection member surface 216. Coupling member 204 is laser welded using a butt-weld to surface 216 of connection members 201. Alternatively, coupling member 204 is attached using other means. Butt-welding coupling member 204 directly to connection members 201 provides an optimal electrical connection between capacitor stack 202 and the feedthrough assembly. Moreover, it also provides for a compact capacitor since very little, if any, space is wasted between capacitor stack 202 and feedthrough assembly 103. Also, since coupling member 204 is directly attached to capacitor stack 202, it helps support feedthrough conductor 203 while a sealing member 105, such as an epoxy, is applied to the feedthrough hole area.

Holding tube 407 is located on the opposing side of base 404 from surface 405. Tube 407 is a cylindrical member having an outer diameter dimensioned to fit within feedthrough hole 107. Tube 407 has a mounting section such as mounting hole 401 defined in part by an inner surface 402 of holding tube 406 which is generally perpendicular to base surface 405. Hole 401 is located down an axial portion of the tube.

Mounting section or hole 401 is for receiving proximal end portion 217 of feedthrough conductor 203. The surface of feedthrough conductor 203 contacts inner surface 402. In the exemplary embodiment, hole 401 is approximately 0.016" (0.4064 mm) in diameter. Alternatively, its diameter can conform with the size of conductor 203 so that feedthrough conductor 203 can matably fit within the hole. In the exemplary embodiment, coupling member 204 has a height 204h of approximately 0.085" (2.519 mm). Other embodiments range from 0.050" to 0.100" or higher. Some embodiments provide a height of greater than 0.100".

Figures 5A, 5B:
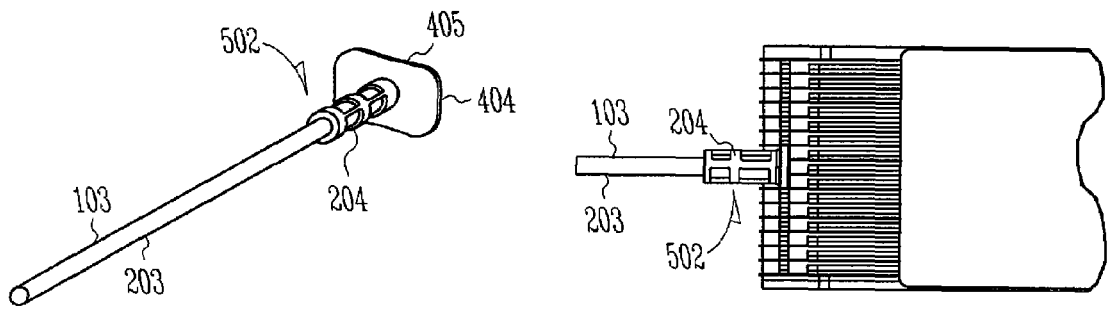
FIG. 5A is an isometric view of the exemplary feedthrough assembly of FIG. 1.
FIG. 5B is a side view of the exemplary feedthrough assembly of FIG. 1.

FIGS. 5A and 5B show an exemplary attachment of feedthrough conductor 203 to coupling member 204. In the exemplary embodiment, feedthrough conductor 203 and coupling member 204 are connected at a crimp 502. Alternatively, they are welded, soldered, glued or interference fit together, as will be discussed below. Exemplary crimp 502 compresses inner surface 402 (see FIG. 4) of tube 407 into mechanical and electrical connection with the surface of portions of feedthrough conductor 203. In the exemplary embodiment, a double crimp is employed. In some embodiments, a single crimp, double crimp, triple crimp or more are used.

In the exemplary embodiment, inner surface 402 of coupling member 204 is a curved surface defining an annular connection member. Crimp 502 compresses and deforms opposing surfaces of annular inner surface 402 to contact conductor 203. In the exemplary embodiment, the opposing surfaces of inner surface 402 are separated by a first distance prior to being crimped and separated by a second distance, smaller than the first distance, after being crimped.

FIG. 7 shows another exemplary coupling member 700. Member 700 includes a base 701 and a holding tube 702. Base 701 is a circular-shaped base. In the exemplary embodiment, base 701 has a diameter of approximately 0.050" (1.27 mm). In one embodiment (not shown), the base is square shaped.

Figures 8A, 8B:
FIG. 8A is an isometric view of another exemplary coupling member in accord with one embodiment of the present invention.
FIG. 8B is an isometric view of another exemplary coupling member in accord with one embodiment of the present invention.

FIG. 8A shows another exemplary coupling member 800. Member 800 does not include a base. In the exemplary embodiment, hole 401 runs completely through holding tube 802. In the exemplary embodiment, one end of tube 802 has a connection surface and is attached to surface 216 of connection members 201. A second end of tube 802 receives feedthrough conductor 203.

FIG. 8B shows another exemplary coupling member 850. Member 850 does not include a base. In the exemplary embodiment, hole 401 runs only partially through a holding tube 852. In the exemplary embodiment, one end of member 850 has a connection surface and is attached to surface 216 of connection members 201. An end of tube 802 receives feedthrough conductor 203.

Figure 9:
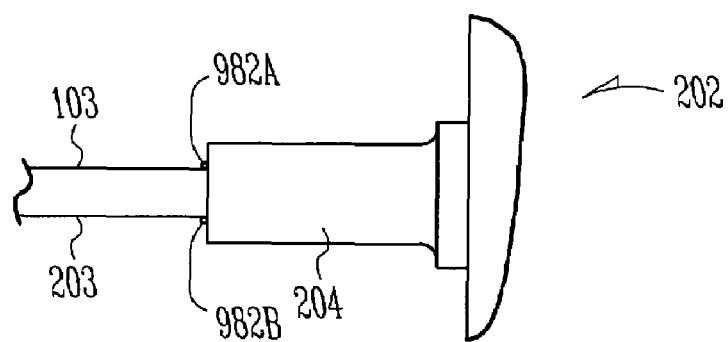
FIG. 9 is a side view of the feedthrough assembly of FIG. 1.

FIG. 9 shows a side view of feedthrough assembly 103 in which feedthrough conductor 203 is coupled to coupling member 204 at one or more arc percussion welding areas, such as areas 982a and 982b. An exemplary arc percussion welding machine is manufactured by Morrow Tech Industries of Broomfield, Colo. In this embodiment, the conductor 203 and coupling members are not crimped together. However, some embodiments include both welding and crimping.

Figure 10:
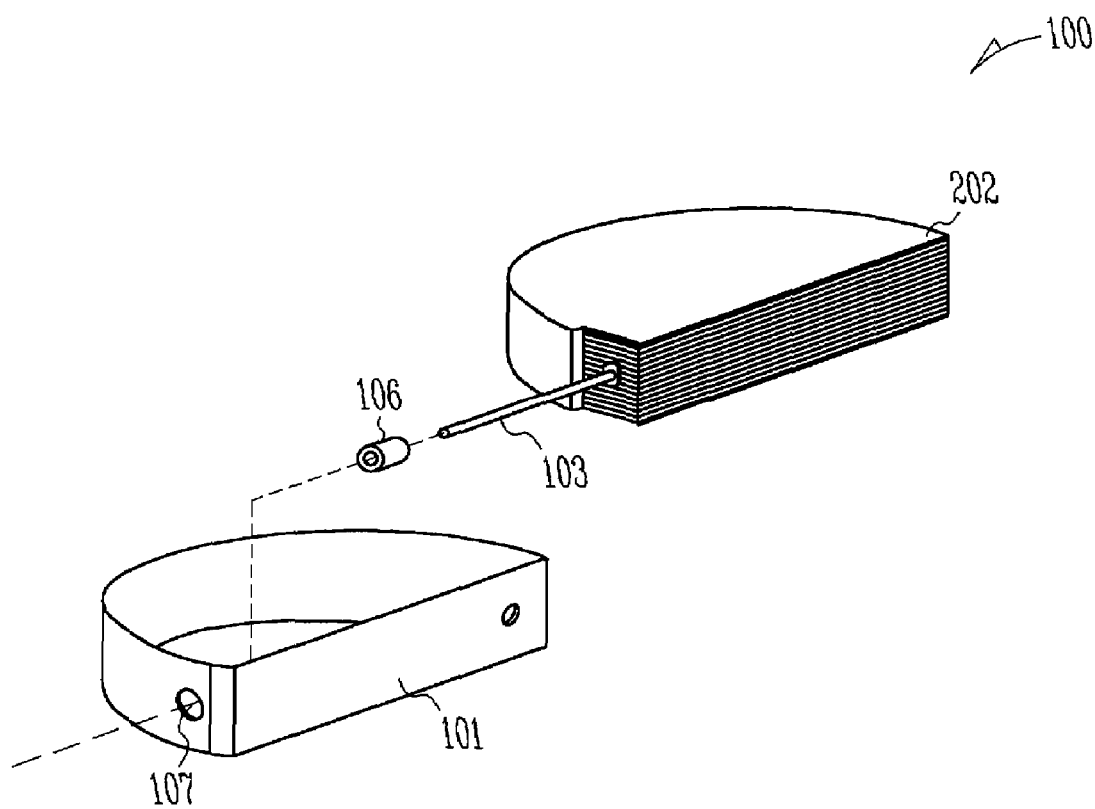
FIG. 10 is an exploded isometric view of a flat capacitor according to one embodiment of the present invention.

FIG. 10 shows an exploded view of capacitor 100 having a sealing member such as a plug 106 according to one embodiment of the present invention. Plug 106 is insertable into feedthrough hole 107 of case 101. In one embodiment, plug 106 has an outer diameter which is larger than the diameter of feedthrough hole 107, and the manufacturer inserts it within hole 107 in an interference fit. When plug 106 is located within feedthrough hole 107, the plug seals feedthrough hole 107 and electrically insulates feedthrough assembly 103 from case 101. In some embodiments plug 106 includes one or more flanges, which will be discussed below.

Figure 11:
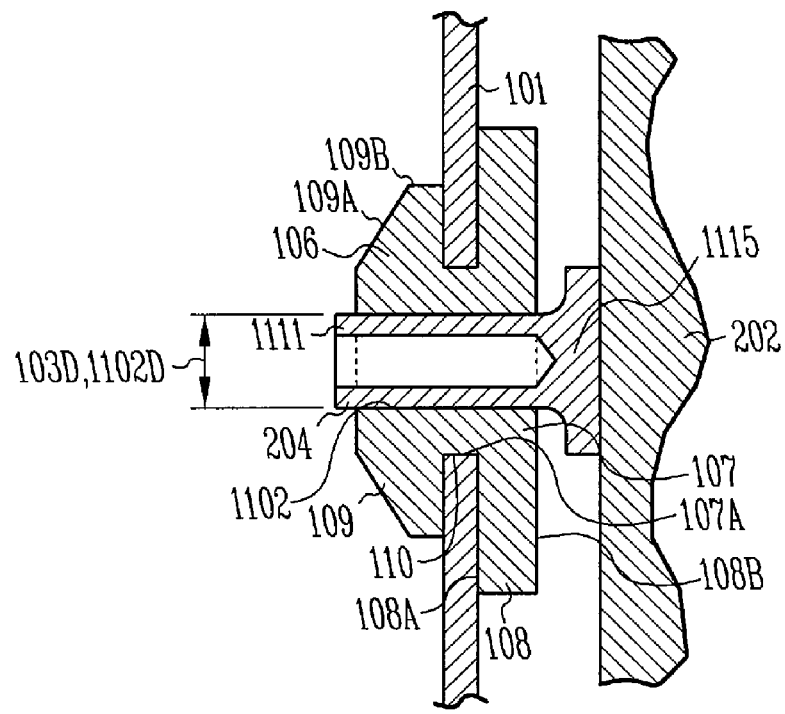
FIG. 11 is a cross-sectional view of the feedthrough assembly of FIG. 10.

FIG. 11 shows a cross-sectional view of plug 106 assembled with capacitor case 101. The present example show coupling member 204 attached to capacitor stack 202. However, in other embodiments plug 106 can also be used in capacitors having other types of feedthrough assemblies. In one embodiment, plug 106 electrically insulates case 101 from coupling member 204. Coupling member 204 has a first end 1115 located in the interior of case 101 and coupled to capacitor stack 202. Coupling member 204 also includes a second end 1111 located exterior to case 101 for connecting to circuitry, such as defibrillator, or other implantable medical device circuitry. In one embodiment, coupling member 204 has a feedthrough terminal attached thereto.

In this embodiment, plug 106 is a double-flanged plug. Plug 106 includes a first flange 108. First flange 108 includes a first surface 108a which faces the inner surface of case 101. When the capacitor begins to become pressurized, pressure against a second surface 108b forces first surface 108a against the case. Thus, flange 108 creates a seal against the inner surface of case 101.

In this embodiment, plug 106 includes a second flange 109. Flange 109 includes a surface which faces the outer surface of case 101.

Plug 106 also includes a plug portion 110 which is located between and defined by first flange 108 and second flange 109. Portion 110 has a smaller diameter than either flange 108 and/or 109. Case edge 107a confronts plug 106 at portion 110. In this embodiment, portion 110 has a normal, unstressed outer diameter approximately equal to the diameter of feedthrough hole 107. In some embodiments, the unstressed outer diameter is larger than the diameter of feedthrough hole 107. In some embodiments, the unstressed outer diameter is smaller than hole 107. As one example, in this embodiment flange 108 has a diameter of approximately 0.080 inches and portion 110 has a diameter of approximately 0.060 inches.

Plug 106 also includes a central passage or hole 1102. In one embodiment, hole 1102 is axially located through the center of plug 106 and has an unstressed diameter 1102d which is smaller than or equal to a diameter 103d of a portion of feedthrough member 103 which is mounted within hole 1102. In various embodiments, diameter 1102d may range from approximately 0.015 inches to approximately 0.033 inches. In other embodiments, diameter 1102d is smaller than 0.015 inches. In some embodiments it is greater than 0.033 inches. Other embodiments vary the hole size depending on the size of the feedthrough conductor used. In some embodiments, when a feedthrough member such as coupling member 204 is inserted through hole 1102, an interference fit seal is developed between the feedthrough member and the plug. In other embodiments, hydrogen gas can escape along the feedthrough member/plug 106 border.

In one embodiment, plug 106 is made from a compressible, elastic material such as rubber, plastic, thermoplastic, or other elastic or elastomeric material. In one embodiment, when plug 106 is mounted within feedthrough hole 107 and feedthrough member 103 is mounted within hole 1102, plug portion 110 is compressed between assembly 103 and edge 107a of feedthrough hole 107 and the plug exerts a radial force on edge 107a of the feedthrough hole. This forces or compresses plug 106 into an interference or compression fit between feedthrough hole edge 107a and member 204, thus helping to seal electrolyte solution within case 101. In other embodiments, the diameter of portion 110 is smaller than hole 107 and an interference fit between feedthrough hole edge 107a and member 204 is not created.

In one embodiment, as noted above, flange 108 provides a sealing means for helping seal electrolyte within the case. Accordingly, in some embodiments, when the diameter of portion 110 is smaller than hole 107 and an interference fit between feedthrough hole edge 107a and member 204 is not created, only flange 108 provides a sealing means between case 101 and plug 106. Advantageously, the seal or seals are formed automatically. Thus, in one embodiment, assembling and tightening a screw or other extraneous hardware is not required to seal the capacitor.

In one embodiment, second flange 109 provides support for mounting plug 106 within hole 107. For instance, when plug 106 is mounted in hole 107, flanges 108 and 109 each help hold plug 106 in place once it is mounted, but before the coupling member 204 is inserted through hole 1102. This aides the manufacturing process.

In one embodiment second flange 109 includes a tapered section wherein an outer portion 109a of flange 109 has a smaller diameter than an inner portion 109b. The tapered shape of flange 109 aids in inserting plug 106 into hole 107. Some embodiments omit the tapered shape and flange 109 has a uniform outer diameter. Other embodiments provide a tapered shape for first flange 108. Other embodiments provide tapered sections on both flanges.

In this embodiment, flange 108 has a larger diameter than flange 109. In some embodiments, the two flanges have substantially equal diameters. In further embodiments, flange 109 has a larger diameter than flange 108.

Some embodiments omit either or both of flanges 108 and 109. For instance, in some embodiments plug 106 has a generally cylindrical shape. In other embodiments, plug 106 has an hour-glass shape or other shape which closely fits within feedthrough hole 107. In some embodiments, plug 106 is a mass of elastic material with a dimension approximately equal to or larger than the width of feedthrough hole 107.

In one embodiment, plug 106 seals the electrolyte within capacitor case 101, but it does not provide a hermetic seal. Hydrogen is created during consumption of water from the electrolyte and continues to be formed throughout the life of the capacitor. This can cause a hermetically sealed capacitor case to bulge outward from the hydrogen gas production within, thus risking long-term device reliability due to shorting.

Accordingly, in one embodiment plug 106 permits outgassing of hydrogen gas, thus alleviating any problems. For instance, in one embodiment, flange 108 creates a seal to the inner wall of the case 101. A pathway for the gas to escape is then present along the border between coupling member 204 and plug 106.

Figure 12:
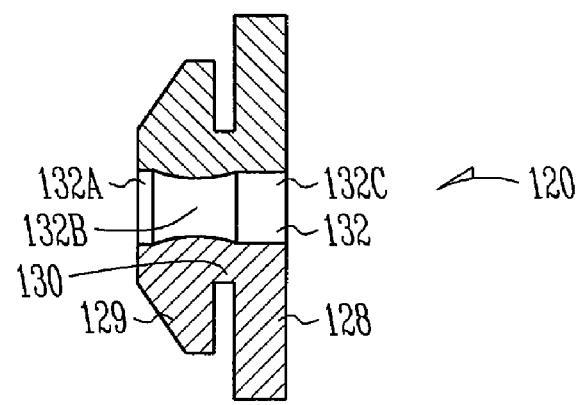
FIG. 12 is a cross-sectional side view showing a feedthrough plug according to one embodiment.

FIG. 12 shows a cross-sectional side view of a plug 120 according to one embodiment. Plug 120 includes one or more features of plug 106 and discussion of unnecessary details will be omitted. Plug 120 includes a first flange 128, a second flange 129, and a portion 130 between the two flanges 128 and 129. In one embodiment, plug 130 includes a hole 132. Hole 132 has a sealing section such as a narrow section 132b, which is located between two nominal diameter sections 132a and 132b. Other embodiments omit section 132b or move it to either end, thereby omitting sections 132a or 132b.

In one embodiment, narrow section 132b provides an O-ring type interference fit for a feedthrough member such as coupling member 204. In this embodiment, narrow section 132b is generally located within second flange 129. Other embodiments locate the narrow section within central portion 130. Other embodiments locate the narrow section within first flange 128. By way of example, in one embodiment, the nominal diameters of sections 132a and 132c is approximately 0.032 inches, and the diameter of narrow section 132b is 0.026 inches.

Referring again to FIG. 10, one method of assembling a capacitor having a plug 106 is as follows. Plug 106 is inserted into feedthrough hole 107 of case 101. In one embodiment, plug 106 includes a double-flange construction which helps hold the plug in place once it is mounted. Feedthrough assembly 103 is attached to capacitor stack 202 and inserted through inner hole 1102 of plug 106 while capacitor stack 202 is placed within the cavity of case 101. An interference fit between plug 106 and feedthrough 103 and between case 101 and plug 106 are created. Thus, a seal is formed between the interior of case 101 and the exterior of case 101.

Exemplary Embodiment of Implantable Defibrillator

Figure 13:
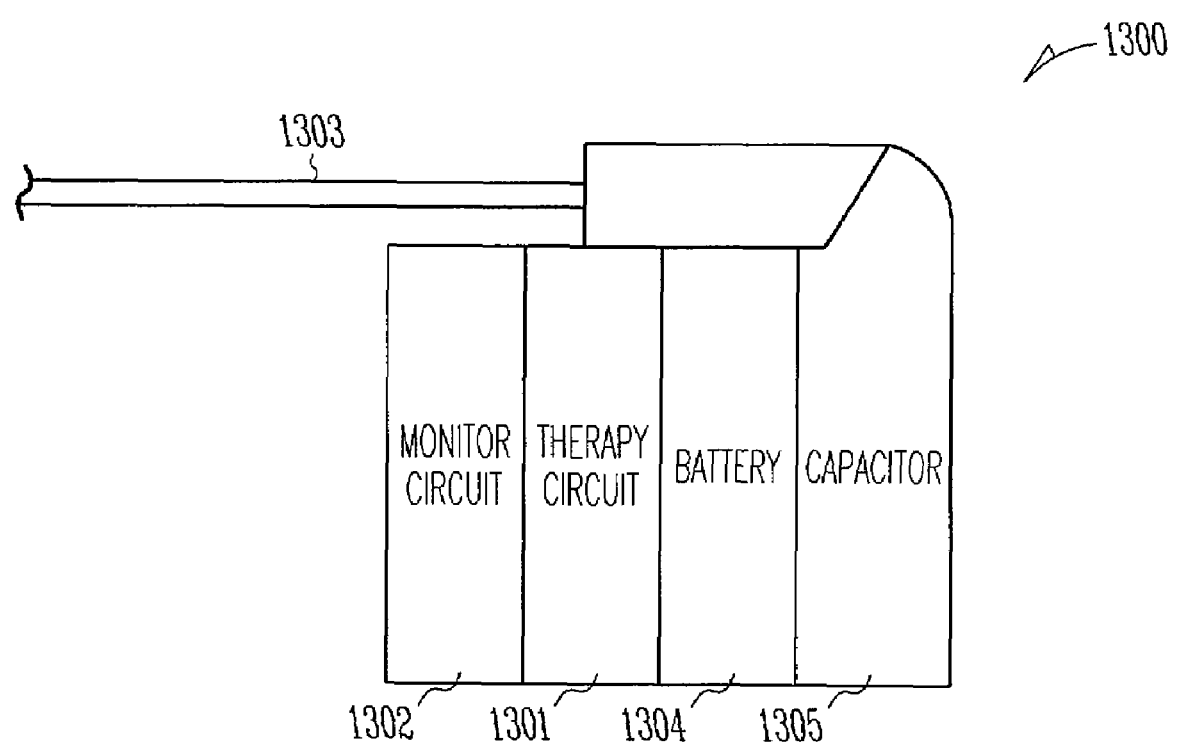
FIG. 13 is a schematic view of an exemplary implantable medical device incorporating a capacitor according to the present invention.

FIG. 13 shows one of the many applications for capacitors incorporating one or more teachings of the present invention: a generic implantable heart monitor 1300. As used herein, implantable heart monitor includes any implantable device for providing therapeutic stimulus to a heart muscle. Thus, for example, the term includes pacemakers, defibrillators, cardioverters, congestive heart failure devices, and combination and permutations thereof.

Heart monitor 1300 includes a lead system 1303, which after implantation electrically contact strategic portions of a patient's heart. Shown schematically are portions of monitor 1300 including a monitoring circuit 1302 for monitoring heart activity through one or more of the leads of lead system 1303, and a therapy circuit 1301 for delivering electrical energy through one or more of the leads to a heart. Monitor 1300 also includes an energy storage component, which includes a battery 1304 and incorporates at least one capacitor 1305 having one or more of the features of the exemplary capacitors described above.

In addition to implantable heart monitor and other cardiac rhythm management devices, one or more teachings of the present invention can be incorporated into photographic flash equipment or other devices using flat or cylindrical capacitors. Indeed, these teachings of the invention are pertinent to any application where high-energy, high-voltage, or space-efficient capacitors are desirable.

CONCLUSION

In furtherance of the art, the inventors have devised a capacitor which includes, in an exemplary embodiment, a coupling member attached to a capacitor stack of the capacitor, a feedthrough conductor attached to the coupling member and extending through the feedthrough hole of the capacitor, and means for sealing the feedthrough hole. One embodiment provides a feedthrough assembly which includes a plug having a hole and a feedthrough conductor mounted within the hole. The feedthrough conductor has a diameter approximately equal to or larger than the plug hole diameter, thus sealing the feedthrough hole without requiring any excess hardware. Among other advantages, the relatively uncomplicated feedthrough structure of the exemplary embodiments provides for easier manufacturing and more reliable capacitors.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A capacitor comprising:
   a case having a feedthrough hole;
   a capacitor stack within the case;
   an elastic plug mounted within the feedthrough hole, the plug having an inner hole; and
   a feedthrough conductor coupled to the capacitor and extending through the plug inner hole, wherein the feedthrough conductor has a larger diameter than an unstressed diameter of the inner hole such that an interference seal fit is formed between the feedthrough conductor and the elastic plug;
   wherein the plug electrically insulates the feedthrough conductor from the case.

2. The capacitor of claim 1, wherein the elastic plug includes a flange confronting an inner surface of the case.

3. The capacitor of claim 1, wherein the capacitor comprises a flat capacitor.

4. The capacitor of claim 1, wherein the feedthrough conductor is directly attached to the capacitor stack.

5. The capacitor of claim 1, wherein the plug has one inner hole.

6. The feedthrough assembly of claim 1, wherein the plug includes a first flange located inside the case and a second flange located outside the case.

7. The feedthrough assembly of claim 1, wherein the feedthrough conductor comprises an aluminum coupling member having a first end extending from a first end of the plug and having a second end extending from a second end of the plug and directly coupled to an active element of the flat capacitor.

8. An implantable medical device comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes one or more capacitors, each capacitor comprising:
   a case having a feedthrough hole;
   a capacitor stack located within the case, the capacitor stack having a top surface and a side surface extending substantially perpendicular from the top surface;
   a coupling member having a base surface flushly abutting the side surface of the capacitor stack and directly attached to the side surface of the capacitor stack, the coupling member having a mounting hole;
   a feedthrough conductor having a portion extending into the mounting hole; and
   a sealing member adjacent the feedthrough hole for sealing the feedthrough hole.

9. The implantable medical device of claim 8, wherein the coupling member comprises a base abutting a surface of the capacitor stack.

10. The implantable medical device of claim 9, wherein the capacitor stack includes two or more connection members, each connection member having an edge face, the surface of the capacitor stack comprises at least one of the edge connection member faces.

11. The implantable medical device of claim 8, wherein the sealing member comprises an elastic plug mounted within the feedthrough hole, the elastic plug having an inner hole, the feedthrough member mounted within the inner hole.

12. The implantable medical device of claim 11, wherein the elastic plug is interference fitted within the feedthrough hole.

13. A method for assembling a capacitor, the method comprising:
   crimping a feedthrough conductor to a coupling member;
   positioning a base surface of the coupling member flushly against an outer surface of a capacitor stack;
   attaching the coupling member to the capacitor stack of the flat capacitor;
   inserting the capacitor stack into a capacitor case so that the feedthrough conductor passes through a feedthrough hole in the capacitor case; and
   sealing the feedthrough hole.

14. The method of claim 13, wherein attaching the coupling member comprises butt-welding the coupling member to a flat connection surface of the active element.

15. The method of claim 13, wherein sealing the feedthrough hole comprises non-hermetically sealing the feedthrough hole by depositing an epoxy around the feedthrough hole.

16. The method of claim 13, wherein sealing the feedthrough hole comprises mounting an elastic insert within the feedthrough hole and inserting a feedthrough conductor through the elastic insert.

17. The method of claim 13, wherein the capacitor stack has a top surface and a side surface extending substantially perpendicular from the top surface and the base surface of the coupling member is positioned flushly against the side surface and attached to the side surface.

* * * * *